United States Patent [19]
Hubbard et al.

[11] Patent Number: 5,458,459
[45] Date of Patent: Oct. 17, 1995

[54] CENTRIFUGAL BLOOD PUMP WITH IMPELLER BLADES FORMING A SPIN INDUCER

[75] Inventors: Lloyd C. Hubbard, Excelsior; Earl W. Clausen, Eden Prairie, both of Minn.

[73] Assignee: Haemonetics Corporation, Braintree, Mass.

[21] Appl. No.: 255,459

[22] Filed: Jun. 8, 1994

Related U.S. Application Data

[63] Continuation of Ser. No. 133,562, Oct. 7, 1993, abandoned, which is a continuation-in-part of Ser. No. 163,393, Dec. 6, 1993, abandoned, which is a continuation of Ser. No. 922,198, Jul. 30, 1992, abandoned.

[51] Int. Cl.⁶ .................................................. F04D 29/04
[52] U.S. Cl. .................................................. 415/206; 415/900
[58] Field of Search .................................. 415/203, 206, 415/900

[56] References Cited

U.S. PATENT DOCUMENTS

| | | | |
|---|---|---|---|
| 3,487,784 | 1/1970 | Rafferty | 415/900 |
| 3,957,389 | 5/1976 | Rafferty et al. | 415/1 |
| 4,507,048 | 3/1985 | Belenger et al. | 415/90 |
| 4,589,822 | 5/1986 | Clausen | 415/900 |
| 4,606,698 | 4/1986 | Clausen | 415/900 |
| 4,643,641 | 2/1987 | Clausen et al. | 415/170 |
| 4,854,820 | 8/1989 | Zolotar et al. | 415/171.1 |
| 4,898,518 | 2/1990 | Hubbard et al. | 417/360 |
| 5,055,005 | 10/1991 | Kletschka | 415/900 |
| 5,147,187 | 9/1992 | Ito et al. | 417/423.1 |
| 5,195,877 | 3/1993 | Kletschka | 417/356 |

Primary Examiner—John T. Kwon
Attorney, Agent, or Firm—Kinney & Lange

[57] ABSTRACT

A centrifugal pump for pumping biological fluids such as blood includes a housing which defines a pumping chamber. The pumping chamber encloses an impeller comprised of a spindle for rotation about a spindle axis and a plurality of blades positioned such that each inner blade end is positioned adjacent to the spindle. The plurality of inner blade ends forms a spin inducer which aids in decreasing hemolysis.

13 Claims, 2 Drawing Sheets

CENTRIFUGAL BLOOD PUMP WITH IMPELLER BLADES FORMING A SPIN INDUCER

This is a continuation application of U.S. patent application, Ser. No. 08/133,562 filed on Oct. 7, 1993, now abandoned, which is a c-i-p of 163,393, filed Dec. 6, 1993, now abandoned, which is a continuation of now abandoned U.S. patent application, Ser. No. 07/922,198 which was filed on Jul. 30, 1992.

BACKGROUND OF THE INVENTION

The present invention relates to pumps and more particularly to centrifugal blood pumps in which impeller blades are positioned so that hemolysis is minimized.

Delicate surgical procedures require that the site of surgery remain motionless. This requirement made early heart surgery difficult to impossible as interruption of the heart's pumping action for the required length of surgical time would invariably be fatal.

During the 1960s, prolonged and non-fatal stoppage of the heart became possible by use of newly developed "heart-lung" machines. These machines consisted of a mechanical blood pump combined with a blood oxygenator. The heart-lung machines were capable of taking over the function of the natural heart and lungs for periods of up to several hours, enabling the development of techniques leading to today's extensive practice of open-heart surgery.

The first practical mechanical blood pumps used were peristaltic or "roller" pumps. The pumping action of a roller pump derives from the compression of a section of the flexible plastic tubing which carries the blood through the heart-lung machine. A moving roller presses the tubing against a semicircular platen, moving the blood forward in the tubing. The speed of the moving roller and the diameter of the tubing control the rate of blood flow.

Although the roller pump was and is simple and reliable, it has two characteristics which can endanger the patient undergoing surgery. First, if flow is inadvertently obstructed, the resulting increase in pressure produced by a roller pump may exceed the bursting strength of the tubing circuit. Second, if air is accidentally introduced into the tubing circuit, it will be pumped to the patient along with the blood. Either of these conditions may result in serious or fatal consequences to the patient.

In 1976, centrifugal blood pumps began to replace the roller pump as the "heart" of the heart-lung machine. The pumping action of a centrifugal blood pump derives from the rotation of an impeller within a pumping chamber. One impeller design associated with centrifugal blood pumps is a disk-shaped device with multiple blades positioned on a surface. The impeller is rotated about a central axis of rotation by way of a rotational drive source. After the blood enters the pumping chamber via an inlet, it makes contact with the impeller blades and is rotated along with the impeller. The impeller rotates at a predetermined speed so that a required pressure and flow rate is maintained.

Pump pressure is controlled by the rotational speed of the impeller. At operational speeds, excessive pressure cannot be produced. Additionally, the centrifugal forces in the pump form a natural air trap and, with massive introduction of air, deprime and discontinue pumping altogether. The above-mentioned safety features, and the decreased blood damage, or hemolysis, caused by centrifugal blood pumps is now widely recognized and has led to their extensive use for open heart surgery.

In the early 1980s it was demonstrated that a mechanical blood pump could be used as a heart-assist pump for patients who could not be separated from the heart-lung machine following surgery. The readily available centrifugal blood pumps were quickly adapted to this situation as well as to the more routine use during heart surgery.

The fragility of blood, however, presents several problems for the design of mechanical blood pumps. Excessive shear forces cause rupture of the red blood cells. Hemolysis is a measure of the rate at which red blood cells are damaged. Despite the risk associated with excessive forces which may cause hemolysis, constant motion and high flow velocity rates are needed (especially over local areas of friction, such as seals) to maintain required pump pressure and to prevent points of high temperature which may cause blood damage and the accumulation of clot deposits. Thus, a balance must be established between adequate rotational speed of the pump impeller and an acceptable level of hemolysis.

Previous centrifugal blood pumps have reduced hemolysis by decreasing the rotational speed of the impeller. The required pump pressure and flow rate of blood in these pumps is maintained by increasing the diameter of the pump. In other words, increasing the diameter counteracts the decrease in rotational speed of the impeller. Some pumps, however, have dimensional constraints which do not allow an increase in pump diameter. A means to reduce hemolysis without increasing the diameter of the centrifugal blood pump is not found in the prior art.

SUMMARY OF THE INVENTION

With the present invention, a reduction in hemolysis is achieved by positioning a plurality of blades of the impeller adjacent to the spindle which intersects the center and is the axis of rotation of the impeller. This configuration reduces hemolysis because the velocity of the blade tangential to the axis of rotation is at its minimum at the center of the impeller. Thus, hemolysis is reduced because the first contact of the blood with the impeller blade occurs at a point where the impeller blades have a relatively low tangential velocity with respect to the axis of rotation. Since the blades of the present invention are positioned adjacent to the center of the impeller, the blood is slowly accelerated from a point of relatively low tangential velocity to a maximum tangential velocity which occurs when the blood reaches the outer blade end.

The present invention is a centrifugal pump for pumping biological fluids such as blood. The pump has a housing which defines a pumping chamber. An impeller, supported by a spindle, rotates about an axis of rotation located at the center of the impeller. The impeller itself is disposed within the pumping chamber. The pumping chamber has an inlet directed at the center of the impeller and an outlet provided along the periphery of the impeller. The impeller includes a plurality of blades positioned on a first surface. An inner end of each blade is adjacent to the spindle which supports the impeller. A plurality of inner blade ends form a cone-shaped area, or spin inducer, around the circumference of the spindle. The location of the spin inducer near the center of the impeller causes the blood to rotate at a relatively low tangential velocity when it enters the high flow inlet area.

The inner ends of the impeller blades, which actually form the cone-shaped spin inducer, are positioned at the center of the impeller adjacent the spindle. The velocity of each inner blade end tangential to the axis of rotation is at a minimum. The spin inducer is able to reduce the amount of hemolysis because the first contact of the blood with the impeller is at a point of relatively low tangential velocity. As the blood continues to travel into the pumping chamber, it is accelerated to a maximum velocity, tangential to the axis of rotation, which occurs at the outer blade end. The gradual acceleration decreases the turbulence of the flow within the pumping chamber and results in less hemolysis than in prior art centrifugal pumps.

DETAILED DESCRIPTION OF THE PREFERRED EMBODIMENTS

Figure 1:
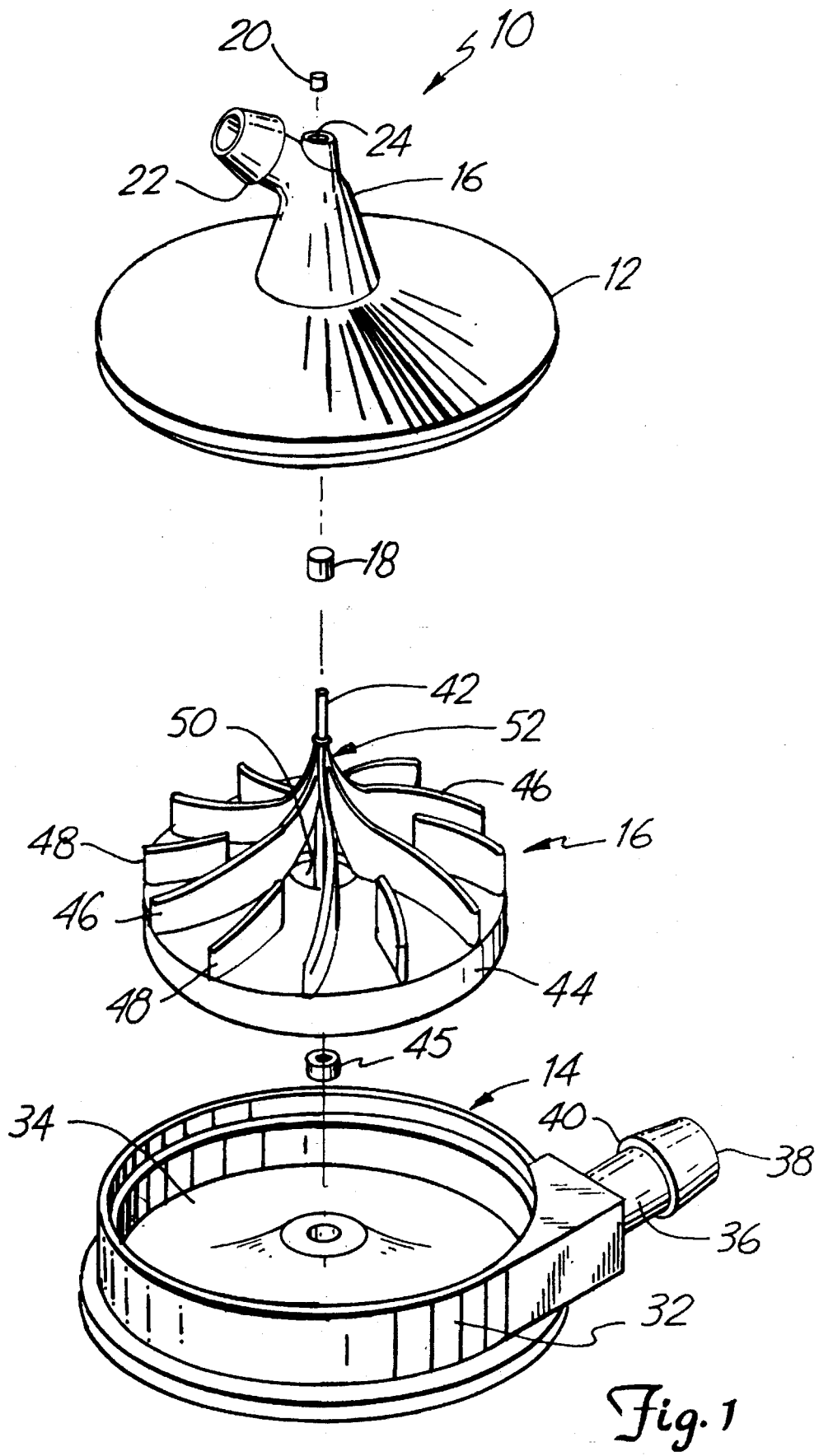
FIG. 1 is an exploded perspective view of the present invention.
Figures 1A, 2:
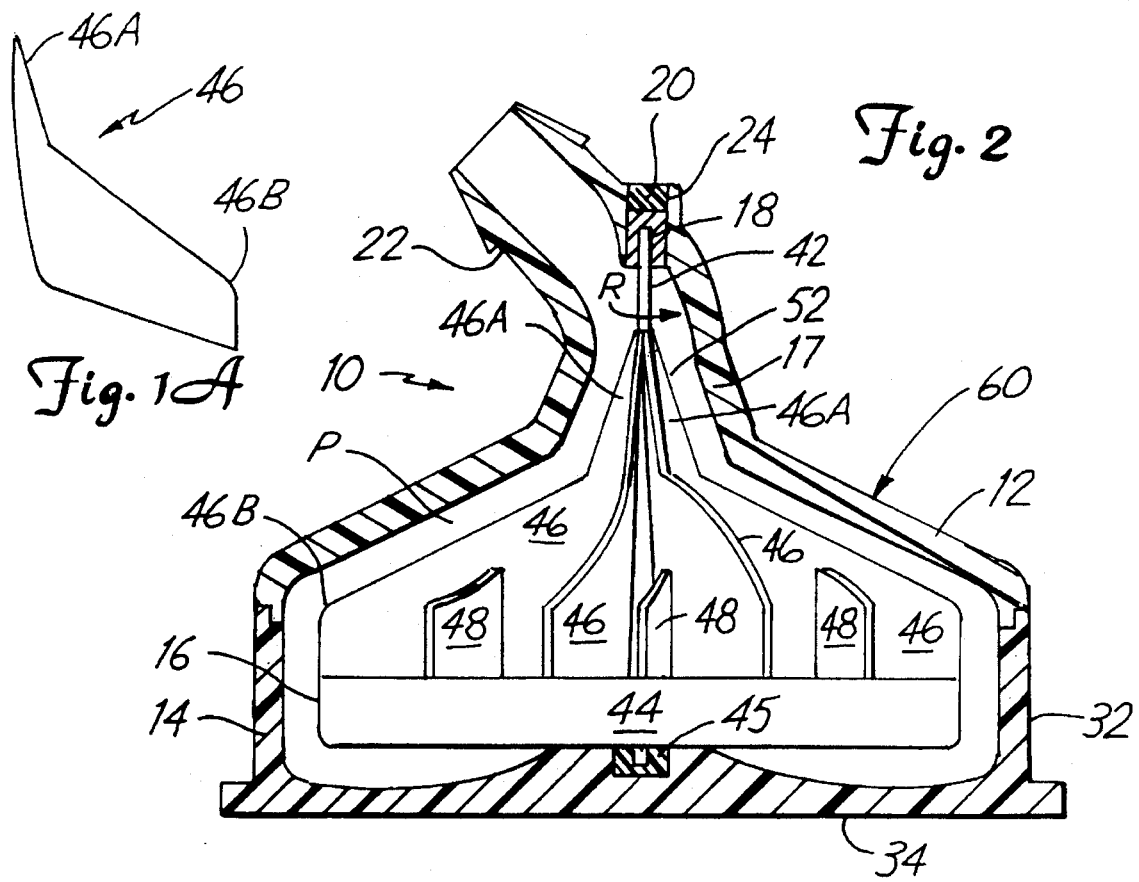
FIG. 1A is a close-up of a full impeller blade.
FIG. 2 is a cross-sectional side view of the present invention.
Figure 3:
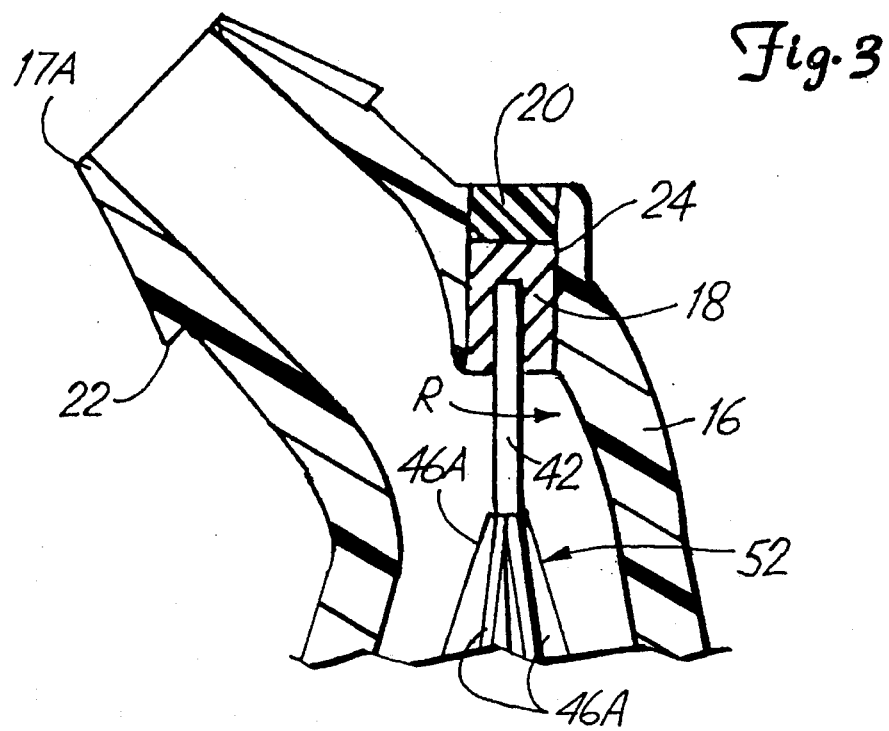
FIG. 3 is a close-up view of the spin inducer shown in the cross-sectional side view of the FIG. 2.

A preferred embodiment of the present invention is shown as centrifugal blood pump 10 in FIGS. 1–3. FIG. 1 shows that blood pump 10 is composed of three distinct parts: upper enclosure 12, base 14, and impeller 16.

Upper enclosure 12 includes inlet 17, journal bearing 18 and plug 20. Ridge 22 on inlet 17 facilitates attachment of inlet tubing (not shown) from a reservoir/oxygenator or from the patient. Journal bearing 18 and plug 20 are mounted in aperture 24 at the bend in inlet 17.

Base 14 includes cylindrical side wall 32, bottom wall 34 and outlet 36. Bottom wall 34 contains aperture 34A in order to receive journal bearing 45. Outlet 36 is a tubular member which extends from cylindrical side wall 32 to free end 38. Ridge 40 facilitates attachment of outlet tubing (not shown) to free end 38.

Impeller 16 includes spindle 42, impeller platform 44, full impeller blades 46 and short impeller blades 48. Central circulation hole 50 and spin inducer 52 are also shown.

FIG. 1A shows a close-up view of full impeller blade 46. Inner blade end 46A and outer blade end 46B are shown. A plurality of inner blade ends 46A forms spin inducer 52 (shown in FIGS. 1, 2 and 3). Full impeller blade 46 is approximately four inches in total length. The width of inner blade end 46A, which is measured laterally from spindle 42 (not shown) to the end of the blade, is approximately 0.25 inches. The width of outer blade end 46B, which is measured vertically from impeller platform 44 (not shown) to the end of the blade, is approximately 0.38 inches. The clearance between inlet 17 and inner blade end 46A is less than the clearance between upper enclosure 12 and outer blade end 46B.

FIG. 2 shows a cross sectional view of centrifugal blood pump 10 as it appears assembled. In this view, housing 60 (formed by upper enclosure 12 and base 14) encloses impeller 16. Pumping chamber P is a volume defined by upper enclosure 12, inlet 17, cylindrical side wall 32 and bottom wall 34.

Impeller 16 is supported by spindle 42 and rotates about an axis of rotation defined by spindle 42 in a direction indicated by arrow R. An inlet end of spindle 42 is inserted into journal bearing 18 while an opposite end of spindle 42 is received by journal bearing 45. Bottom wall aperture 34A (shown in FIG. 1) receives journal bearing 45. Attached to platform 44 are full impeller blades 46 and short impeller blades 48. Full blades 46 extend across platform 44 and central. circulation hole 50 (shown in FIG. 1 ). Short blades 48 have a length approximately half the radius of platform 44. Both full blades 46 and short blades 48 are tapered. Inner blade ends 46A are supported by and positioned adjacent spindle 42 to form cone-shaped spin inducer 52.

Platform 44 has positioned on its bottom surface, magnets (not shown), which are coupled with magnets carried by a drive rotor (not shown) positioned below bottom wall 34 of base 14. In this configuration of a centrifugal blood pump, an electric motor is connected to the rotor in order to rotate the magnets on the bottom of platform 44 which are coupled with the magnets on the rotor. Both magnets on platform 44 and the rotor rotate about the axis of rotation. The magnets on the bottom of platform 44 and the magnets carried by the rotor are coupled together so that the impeller rotates at the same speed as the rotor.

In another configuration, the impeller is mounted on a drive shaft which extends outside the pumping chamber to a rotational drive source. As the drive source is activated, the .impeller rotates along with the shaft. In either configuration, however, rotational speed adequate to create the required pump pressure and rate of flow of blood must be maintained.

Blood from the patient enters inlet 17 and is directed toward spin inducer 52. At this point, blood flow is generally in the axial direction. Journal bearing 18 receives an end of spindle 42. Journal bearing 18 is press-fit into aperture 24 and is capped with epoxy plug 20. Impeller 16 is supported by spindle 42. While impeller 16 is rotated by methods discussed above, blood contacts spin inducer 52 and experiences gradual acceleration as it travels through pumping chamber P. Full impeller blades 46 and short impeller blades 48 cause the blood to circulate within pumping chamber P toward outlet 36.

FIG. 3 shows a close-up view of a portion of inlet 17 and inner blade ends 46A, which form spin inducer 52. Spin inducer 52 is supported by spindle 42. Journal bearing 18 is shown press-fit into aperture 24 and capped with epoxy plug 20. Inlet tubing (not shown) is secured by ridge 22 and extends away from inlet 17.

High shear rate and turbulence can cause rupture (hemolysis) of the red blood cells Therefore, it is desirable to accelerate the blood cells slowly so that there is no drastic change in speed or in flow direction of the blood. Unlike the bladed impellers found in prior art centrifugal blood pumps, spin inducer 52 serves to reduce the impact of the turbulent flow which is normally associated with the inlet area. Specifically, spin inducer 52 acts as a means to slowly accelerate the blood. The tangential velocity of inner blade ends 46A, which form spin inducer 52, is less than the tangential velocity of outer blade ends 46B. Although the rotational speed remains constant at all points on impeller 16, the tangential velocity of the blade decreases as one moves toward the center of impeller 16.

Hemolysis is reduced because the relatively slow tangential velocity and acceleration of the blood as it enters inlet 17 and impacts spin inducer 52 causes less blood damage than prior art pumps which do not have a spin inducer.

Positioning impeller blades such that spin inducer 52 is formed allows for the blood to travel in a manner such that dramatic increases in tangential velocity (i.e. acceleration) do not occur. Thereby, the blood experiences less turbulence in the high flow inlet area and hemolysis is reduced.

In an alternative embodiment of the present invention, the inlet may be vertical instead of the curved shape shown in FIGS. 1–3. In this configuration, the spindle is inserted into a journal bearing which is supported by struts which extend from the inlet wall. Similar to the embodiment shown in FIGS. 1–3, however, the inlet is flared so that the spin inducer may fit inside.

Although the present invention has been described with reference to preferred embodiments, workers skilled in the art will recognize that changes may be made in form and detail without departing from the spirit and scope of the invention.

What is claimed is:

1. A centrifugal pump for pumping biological fluids such as blood, adapted to be coupled with a source of rotation, the pump comprising:

a housing defining a pumping chamber, the housing having an inlet and an outlet; and an impeller coupled with the source of rotation, the impeller comprising:

a rotatable spindle enclosed within the pumping chamber for rotation about a spindle axis of rotation, the spindle comprising an inlet end rotatably supported from the housing and a base end rotatably supported from the housing, opposite the inlet end;

a plurality of blades supported on the spindle, wherein the blades and the spindle rotate together about a spindle axis of rotation, each blade having an inner blade end and an outer blade end, the inner blade ends having a radial distance from the spindle axis to an outer most edge of the inner blade ends which is substantially less than a radial distance from the spindle axis to an edge of the outer blade ends in the pumping chamber; and a spin inducer formed by the inner blade ends and extending into the inlet wherein the inner blade ends and spindle rotate together about the spindle axis with a significantly lower tangential velocity than the outer blade ends of the impeller, for gradual acceleration Of biological fluids entering the pumping chamber through the inlet without excessive turbulence and shear forces.

2. The centrifugal pump of claim 1 wherein the impeller blades are tapered.

3. The centrifugal pump of claim 1 wherein the impeller further includes a plurality of short blades which do not contact the spindle.

4. The centrifugal pump of claim 1 wherein the spin inducer has a conical shape.

5. In a centrifugal pump for pumping biological fluids of the type having a housing which defines a pumping chamber with an inlet and an outlet and an impeller coupled to a source of rotation, the impeller comprising a rotatable spindle for rotation about a spindle axis and a plurality of blades, each blade having an inner end and an outer end, the improvement comprising:

a spin inducer, located within the inlet, formed by a plurality of inner blade ends of the impeller, wherein the inner blade ends have a radial distance from the spindle axis to an outer most edge of the inner blade ends which is substantially less than a radial distance from the spindle axis to an edge of the outer blade ends in the pumping chamber, the spin inducer positioned adjacent to a center of the impeller, wherein the inner blade ends are attached to the spindle such that the inner blade ends and spindle rotate together about the spindle axis with a significantly lower tangential velocity than the outer blade ends of the impeller, for gradual acceleration of biological fluids without excessive turbulence and shear forces.

6. The centrifugal pump of claim 5 wherein the blades are tapered so that the inner end of the blade has a width which is less than the width of the outer end of the blade.

7. The centrifugal pump of claim 6 wherein the spin inducer extends into the inlet.

8. The centrifugal pump of claim 5 wherein the inner blade ends have a radial distance from the spindle axis to an outer most edge of the inner blade ends which is less than a quarter of the radial distance from the spindle axis to an edge of the outer blade ends in the pumping chamber.

9. The centrifugal pump of claim 5 wherein clearance between the inlet and the inner blade ends is less than clearance between the housing of the pumping chamber and the outer blade ends.

10. A centrifugal pump for pumping biological fluids such as blood, the pump comprising:

a housing defining a pumping chamber with an inlet and an outlet;

a rotatable spindle enclosed within the pumping chamber for rotation about a spindle axis of rotation, the spindle having first end extending into the inlet and a second end;

a disk-shaped platform which supports the plurality of blades; and a plurality of tapered blades each having an inner blade end located within the inlet adjacent to the first end of the spindle and an outer blade end extending away from the spindle and located closer to the second end of the spindle than the inner blade end, the inner blade ends having a radial distance from the spindle axis to an outer most edge of the inner blade ends which is substantially less than a radial distance from the spindle axis to an edge of the outer blade ends in the pumping chamber wherein the plurality of tapered blades and the spindle rotate together about the spindle axis of rotation the inner blade ends and spindle rotating together with a significantly lower tangential velocity than the outer blade ends of the impeller, for gradual acceleration of biological fluids without excessive turbulence and shear forces.

11. The centrifugal pump of claim 10 and further comprising a second plurality of blades which are positioned on the platform, the second plurality of blades extending a partial distance between an outer periphery of the platform and the spindle.

12. The centrifugal pump of claim 10 wherein the blades are tapered such that a width of the inner blade ends is less than a width of the outer blade ends.

13. The centrifugal pump of claim 11 wherein the platform includes a central circulation hole.

* * * * *

UNITED STATES PATENT AND TRADEMARK OFFICE
CERTIFICATE OF CORRECTION

PATENT NO. : 5,458,459

DATED : October 17, 1995

INVENTOR(S) : LLOYD C. HUBBARD, EARL W. CLAUSEN

It is certified that error appears in the above-indentified patent and that said Letters Patent is hereby corrected as shown below:

Col. 4, line 4, delete ".", before circulation.

Col. 4, line 23, delete ".", before impeller.

Col. 5, line 37, delete "Of", insert --of--

Signed and Sealed this

Second Day of January, 1996

Attest:

BRUCE LEHMAN

Attesting Officer

Commissioner of Patents and Trademarks